United States Patent [19]

Cooke

[11] 4,158,611
[45] Jun. 19, 1979

[54] PROCESS FOR RECOVERING CRUDE PHENOL FROM CATALYST-FREE CUMENE HYDROPEROXIDE CLEAVAGE REACTION PRODUCTS

[75] Inventor: Maurice D. Cooke, East Horsley, England

[73] Assignee: BP Chemicals Limited, London, England

[21] Appl. No.: 860,859

[22] Filed: Dec. 15, 1977

[30] Foreign Application Priority Data

Dec. 18, 1976 [GB] United Kingdom ............... 48075/76

[51] Int. Cl.$^2$ ................... B01D 3/00; C07C 37/38
[52] U.S. Cl. ........................................ 203/28; 203/35;
203/43; 203/49; 203/77; 203/80; 203/81;
203/DIG. 9; 203/DIG. 19; 568/754; 202/155
[58] Field of Search ........... 260/621 A, 621 C, 627 R,
260/593 A, 593 P, 621 L, 593 A, 593 P;
568/754, 749; 203/DIG. 19, 99, 71, 81, 74, 77,
28, 29, 49, 91, 80, 35, 42, 43, DIG. 9; 202/155

[56] References Cited

U.S. PATENT DOCUMENTS

| 2,720,549 | 10/1955 | Armstrong et al. | 568/754 |
| 2,734,085 | 2/1956 | Adams et al. | 568/754 |
| 2,824,048 | 2/1958 | Hupe et al. | 568/749 |
| 2,910,511 | 10/1959 | Joris | 568/754 |
| 2,992,169 | 7/1961 | Gregory et al. | 568/754 |
| 3,180,897 | 4/1965 | Sodomann et al. | 568/754 |
| 3,215,745 | 11/1965 | Frank | 568/754 |
| 3,436,429 | 4/1969 | Flickinger et al. | 568/749 |

FOREIGN PATENT DOCUMENTS 1107661 4/1956 France ..................... 568/754

Primary Examiner—Wilbur L. Bascomb, Jr.
Attorney, Agent, or Firm—Brooks, Haidt, Haffner & Delahunty

[57] ABSTRACT

Crude phenol is recovered from CHP reaction products by continuously feeding to a main column separating in its uppermost section phenol from crude acetone, this fraction being removed overhead, and in the lower section crude phenol from higher boilers, including acetophenone and carbinol, the crude phenol being removed as a sidestream fraction from the main column at a point in the column above the feed-point wherein the total concentration of acetophenone plus carbinol is less than 1,000 ppm and the higher boiling compounds being removed as a base fraction.

13 Claims, 1 Drawing Figure

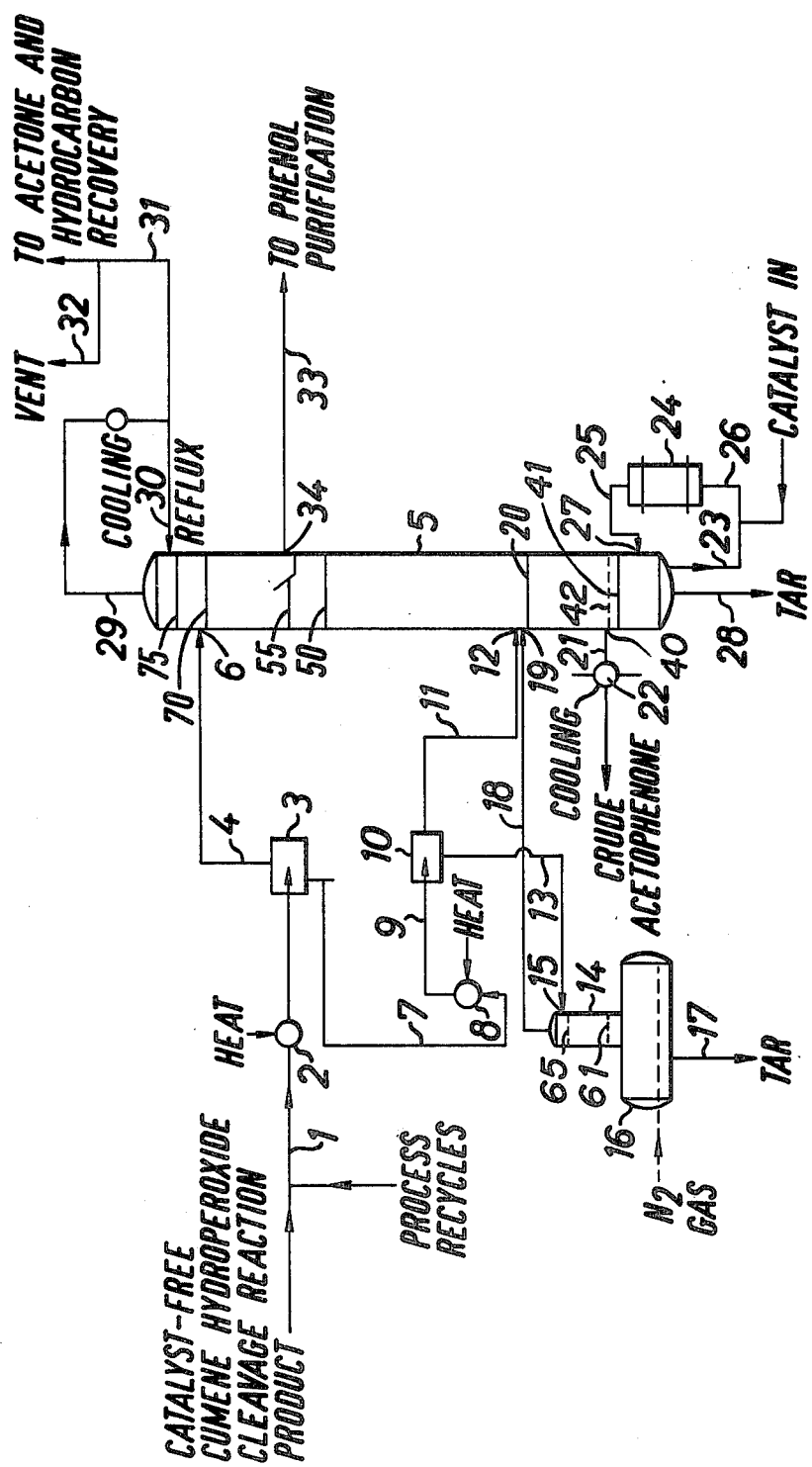

PROCESS FOR RECOVERING CRUDE PHENOL FROM CATALYST-FREE CUMENE HYDROPEROXIDE CLEAVAGE REACTION PRODUCTS

The present invention relates to the production of phenol and in particular to a process for recovering phenol from the reaction mixture obtained by the cleavage of cumene hydroperoxide.

An efficient industrialised method for producing phenol on a large scale is by the oxidation of isopropyl benzene, otherwise known as cumene, to cumene hydroperoxide, which is thereafter subjected to a cleavage reaction, generally in the presence of an acid catalyst to produce, as principal products, phenol and acetone. In addition to the principal products there are formed varying amounts of side-products such as mesityl oxide, alpha-methyl styrene, alpha-methyl styrene dimers, para-cumyl phenol, phenyl dimethyl carbinol (carbinol), acetophenone, other high phenols and high-boilers. The cleavage product together with any un-reacted cumene, to be referred to hereinafter as the cumene hydroperoxide cleavage reaction product, after removal of any catalyst which may be present, is fed to a distillation column, hereinafter referred to as a crude acetone column wherein there is removed an overhead fraction containing all material in the feed with a boiling point lower than that of phenol including acetone, water, most of the mesityl oxide, cumene and alpha-methyl styrene in addition to the practical minimum content of phenol, normally below 1%, which fraction will hereinafter be referred to as the crude acetone fraction. Acetone is recovered from the crude acetone fraction in a series of fractional distillations wherein there are also recovered cumene, which is recycled to the oxidation and alpha-methyl styrene which is hydrogenated and returned to the oxidation as cumene.

Taken from the bottom of the crude acetone column is a fraction containing phenol, carbinol, acetophenone, higher phenols, α-methyl styrene dimers and high-boilers, which is fed to a distillation column, hereinafter referred to as a crude phenol column wherein there is removed an overhead fraction, to be hereinafter referred to as the crude phenol fraction, containing phenol and less than 1,000 ppm (weight) in total of acetophenone and carbinol and a fraction containing phenol, acetophenone, carbinol and high-boilers is removed as a bottoms fraction. It is customary to feed the bottoms fraction from the crude phenol column to a cracking zone maintained at a temperature of, for example, 300°–400° C.

In the cracking zone higher-boiling compounds present are partially decomposed to phenol and hydrocarbons which are removed, together with acetophenone and uncracked material as a vapour fraction. This fraction is fed to an acetophenone column wherein an overhead fraction containing phenol and hydrocarbons is separated from acetophenone and other high-boiling compounds and returned to the crude acetone column.

The crude phenol fraction separated overhead in the crude phenol column is subjected to further treatment in order to recover phenol of the desired purity.

It has now been found that the internal reflux ratio, defined as the ratio of the number of moles of liquid downflow to number of moles of vapour upflow, required to separate crude acetone from phenol in the top section of the crude acetone column is substantially equal to the internal reflux ratio necessary for separation of crude phenol from acetophenone and carbinol, which is the operation performed by the crude phenol column, particularly when the crude phenol is removed as a liquid sidestream from the column. In view of this it is possible to combine the two operations in a single column wherein crude phenol is removed as a sidestream containing small amounts of hydrocarbon (generally up to about 3 wt %) plus other lower-boiling impurities, thereby saving both equipment costs and utilities consumption.

Thus according to the present invention there is provided a process for recovering crude phenol from catalyst-free cumene hydroperoxide cleavage reaction product which process comprises continuously feeding the product to an intermediate point in a column provided with conventional reboiler, condensing and refluxing facilities, hereinafter referred to as the main column, separating in the upper section thereof phenol from a crude acetone fraction as hereinbefore defined, this fraction being removed as an overhead fraction from the head of the upper section, and in the lower section thereof separating crude phenol, as hereinbefore defined, from a fraction containing materials of higher-boiling point than phenol, including acetophenone and carbinol, the crude phenol being removed as a sidestream fraction from the main column at a point in the column above the feed-point wherein the total concentration of acetophenone plus carbinol in the phenol is reduced by fractionation to less than 1,000 ppm (weight), and removing at the base of the main column a fraction containing acetophenone, carbinol, phenol and higher-boiling compounds.

Whilst the main column may be operated over a wide range of pressures it will be found most convenient to operate at atmospheric pressure.

Substantially pure acetone may be recovered from the crude acetone fraction removed as an overhead fraction from the head of the upper section by industrialised methods.

The crude phenol is preferably removed from the main column as a liquid sidestream fraction but may, at the expense of additional heat input, be separated as a vapour sidestream.

The crude phenol sidestream fraction may contain, in addition to phenol and less than 1,000 ppm of acetophenone plus carbinol, lower-boiling impurities than phenol eg., acetone, water and hydrocarbons such as cumene and alpha-methyl styrene. Phenol of any required purity up to the high-purity required for bisphenol resins and pharmaceuticals may be recovered from this sidestream fraction by industrialised methods. The low-boilers present in the crude phenol may be separated and recycled to the main column.

Whilst the catalyst-free cumene hydroperoxide cleavage reaction product fed to the main column generally contains phenol, acetone, water, cumene, mesityl oxide, alpha-methyl styrene, phenol dimethyl carbinol, acetophenone, higher phenols, α-methyl styrene dimers and other high-boiling compounds it may include, in addition, various recycle streams from downstream distillations. The product together with any recycle streams may be almost completely vaporised prior to being fed to the main column. Vaporisation may be accomplished in one or more stages. Preferably vaporisation is carried out in a plurality of stages wherein each stage is effected at a progressively increasing temperature, the first stage being carried out at a temperature above the boiling point of acetone but below the boiling point of phenol to give a vapour fraction mainly consisting of compounds boiling below phenol, including a substantial proportion of acetone and containing, in addition, traces of acetophenone plus carbinol as well as phenol and a residue fraction containing phenol and higher boiling compounds. Provided that the total concentrations of acetophenone plus carbinol in the vapour fraction is consistent with the removal from the main column of a crude phenol sidestream fraction containing less than 1,000 ppm (weight) of acetophenone plus carbinol, the vapour fraction may be fed directly to the main column at a point in the column above the crude phenol sidestream fraction removal point. When the concentration of acetophenone plus carbinol is in excess of this amount it may be reduced by light fractionation before the vapour fraction is fed to the main column. It is then preferred to pass the higher-boiling residue fraction containing the bulk of the phenol to a second vaporisation stage maintained at a temperature above the boiling point of phenol to give a vapour fraction containing the bulk of the phenol which may be fed to the main column at a point in the base region of the lower section thereof, hereinafter referred to as the main feed point. The unvaporised portion from the second stage vaporisation may be treated in any convenient manner. For example it may be pyrolised at a temperature above about 300° C. and the decomposition products fed to the main column. Alternatively the crackable high-boiling compounds such as ortho- and para-cumyl phenols and -methyl styrene dimers present in the unvaporised portion from the second stage vaporisation may be removed and fed to the main column at, for example, the main feed-point. The crackable high-boiling compounds may be removed by such methods as stripping under reduced pressure or stripping in the presence of an inert gas such as nitrogen. This method of operation has the advantage that it prevents any salts present in the cumene hydroperoxide cleavage reaction product from entering the main column. As a further alternative it is also possible to submit the unvaporised portion from the second stage vaporisation to a wash treatment, eg, with acidified aqueous sodium sulphate solution to remove the bulk of any salts present and thereafter to feed the unvaporised portion to the main column. A further advantage will only be realised when operated in combination with an embodiment to be described hereinafter.

As hereinbefore described it is possible to employ a single column because the internal reflux ratio required at the top of the column for separation of crude acetone from higher-boiling materials matches the internal reflux ratio below a crude phenol side draw-off point for separation of crude phenol from higher-boiling material in the feed, particularly if the crude phenol is removed as liquid rather as vapour. In a typical operation the catalyst-free cumene hydroperoxide cleavage reaction product may contain up to about 30,000 ppm (by weight) of acetophenone plus phenyl dimethyl carbinol. The internal reflux ratio required for the separation of this comparatively small amount of high-boiling impurity is of the order of 0.5 when the column liquid and vapour flows are based only on the phenol, acetophenone and carbinol undergoing separation. The required reflux ratio does, however, depend on the column operating pressure and on the amount of lower-boiling materials, acetone, water and cumene, present in the fractionating zone. In addition the internal reflux ratio depends on the number and efficiency of the fractionating trays provided between the feed-point and sidestream removal point and on the degree of separation required. Typically, with 35 fractionating trays above the main phenol feed-point operating at about 60% overall efficiency and with a means pressure of about 1,000 millimeters mercury absolute in the fractionating zone and with about 50 mole % of low-boiling material in the catalyst-free cumene hydroperoxide cleavage reaction product feed at the main feed-point to the main column an internal reflux ratio of about 0.55 (based only on phenol), acetophenone and carbinol) is adequate for reducing the concentration of the acetophenone plus carbinol present in the feed to below about 200 ppm in the liquid phenol sidestream fraction removed at about 173° C. from the main column. The re-boiler at the base of the main column provides a controlled vapour flow in addition to that supplied by the feed vaporisation in order to provide the reflux ratio necessary.

Because crackable high-boiling compounds may be fed to the main column it is particularly preferred to extend the lower section of the main column below the main feed-point and withdraw crude acetophenone as a secondary minor sidestream fraction from a point towards the base of the extended section, thereby allowing concentration of the remaining higher-boilers in the reboiler at the base of the column. Such a modification is equivalent to the operation carried out in the acetophenone column hereinbefore referred to. At the same time it permits sufficiently high temperatures in the reboiler to facilitate catalysed decomposition of the higher-boiling compounds therein. It is therefore preferred to introduce a cracking catalyst into the reboiler maintained at a temperature above 250° C. and preferably less than 300° C. The cracking catalyst may be non-acidic. Preferably the catalyst is phosphoric acid in concentration of about 0.1 wt. %. This mode of operation concentrates the thermal decomposition in the reboiler of the extended main column and the comparatively low temperature required to crack high-boiling compounds in the presence of a cracking catalyst results in less tar formation.

The invention will now be illustrated by reference to the following Example and the attached Drawing which is in the form of a flow diagram illustrating a preferred embodiment of the invention.

EXAMPLE

The principal items of equipment identified in the FIGURE will now be described.

5 is a continuously operated column containing a total of 75 fractionating trays operating with atmospheric pressure at its vent. The column is provided with a reboiler 24 and conventional overhead condensing and refluxing arrangements. The heat input to the reboiler 24 is controlled to provide a reflux to product ratio of crude acetone distillate fraction of about 0.9:1, calculated at the top tray temperature of about 90° C. The reflux flow is modulated by a controller to maintain a temperature of about 105° C. at the third tray from the top of the column. This controlled temperature is monitored by analysis of the phenol content of the distillate and is adjusted accordingly. 14 is a stripping column containing a total of five trays. This column surmounts a residue stripping vessel 16, having a heat input facility plus provision for sparging nitrogen gas, operated at about 300° C. to minimise thermal cracking of the residue. 22 is a condenser for condensing acetophenone vapour from tray 42.

A feed stream composed of cumene hydroperoxide cleavage reaction product free from catalyst and containing various process recycle streams, having the following approximate composition with regard to major constituents:

| Component | Kg./hr |
|---|---|
| Acetone | 9924 |
| Water | 2834 |
| Hydrocarbon (cumene + alpha methylstyrene) | 4638 |
| Phenol | 12166 |
| Higher-boilers includng cumyl phenols | 890 |
| | 30452 | and containing between about 10,000 and 30,000 ppm by weight of acetophenone plus phenyl dimethyl carbinol, to be referred to hereinafter as carbinol, was fed through line 1 to the first stage vaporiser 2 maintained at a temperature of about 90° C. In the vaporiser 2 about 30 wt % of the feed was vaporised and from the separator 3 an acetone-rich vapour fraction containing less than about 500 ppm by weight of acetophenone plus carbinol was removed and passed through line 4 to enter the main column 5 at point 6, five trays below the top of the column. The unvaporised portion of the feed was passed from the separator 3 through line 7 to the second stage vaporiser 8 operated at a temperature of 193° C. and then through line 9 to the separator 10. The vaporised portion containing the bulk of the phenol in the feed was passed through line 11 to enter the main column 5 at point 12 corresponding to fractionating tray 20 from the base of the column. The unvaporised portion containing a small proportion of phenol and higher-boiling compounds was passed through line 13 to the top of the residue stripping column 14 at point 15. Accumulated tar was intermittently removed from the base of the residue stripping vessel 16 through line 17. Vaporised phenol and any vaporised pyrolysis products together with some undecomposed high-boiling compounds and nitrogen were passed through line 18 to enter the main column at point 19, twenty trays above the base of the column.

A crude acetophenone fraction containing higher- and lower-boiling impurities was removed as a small sidestream vapour fraction from the main column 5 at point 40, two or three trays above the base of the column, and fed through line 21 to the condenser 22.

Taken from the base of the column 5 through line 23 was a residue stream containing those higher-boiling compounds remaining after removal of the acetophenone sidestream through line 21. This stream was continuously circulated through the reboiler 24 and returned to the base of the column below tray 41 via line 25. Phosphoric acid was added to the reboiler through line 26 in an amout sufficient to result in a concentration of about 0.1% w/w in the liquid circulating through the reboiler 24. The temperature at the exit of the reboiler was maintained in the range 250°-300° C. by controlling the acetophenone sidestream removed through line 21. In the reboiler high-boiling compounds were cracked to lower-boiling compounds which were returned to the main column through line 25. Tarry material formed in the reboiler 24 was removed, when ncessary, as a small bleed from the base of the main column 5 through line 28.

A distillate fraction containing lower-boiling compounds than phenol including a substantial proportion of acetone was removed from the top of the main column 5 through line 29, part being returned through line 30 as reflux and the remainder having the following composition being removed through line 31 for purification by conventional means. Nitrogen was vented through line 32. Phenol and hydrocarbon recovered during purification were recycled.

| Composition and hourly flow of the crude acetone distillate in terms of major constituents removed through line 31 | |
|---|---|
| Acetone | 9517 Kg/hr |
| Water | 2849 Kg/hr |
| Hydrocarbon (cumene + alpha methylstyrene) | 4496 Kg/hr |
| Phenol | 150 Kg/hr |
| Total | 17012 Kg/hr |

A crude phenol fraction containing less than 1000 ppm (by weight) of acetophenone+carbinol was removed from the main column 5 through line 33 at a point 34, 55 trays above the column base. The composition and hourly flow of the sidestream fraction with regard to major constituents was as follows:

| | |
|---|---|
| Acetone | 407 Kg/hr |
| Hydrocarbon (cumene and alpha methylstyrene) | 500 Kg/hr |
| Phenol | 12184 Kg/hr |
| Total | 13091 Kg/hr |

High purity phenol may be recovered from this sidestream fraction by methods well-known in the art. The low-boiling impurities are eventually recovered and recycled to the feed to the main column 5.

I claim:

1. A process for recovering crude phenol from catalyst-free cumene hydroperoxide cleavage reaction product which process comprises continuously feeding said reaction product to an intermediate point in a distillation column provided with conventional reboiler, condensing and refluxing facilities, separating in the upper section of said distillation column phenol from a fraction containing materials having a boiling point lower than phenol, including acetone, said fraction being removed as an overhead fraction from the head of said upper section, and in the lower section of said distillation column separating crude phenol from a fraction containing materials of higher boiling point than phenol, including acetophenone and carbinol, said crude phenol being removed as a sidestream fraction from said column at a point in said column above said feed-point wherein the total concentration of acetophenone plus carbinol in said crude phenol is reduced by fractionation to less than 1000 ppm (weight), and removing at the base of said column a fraction containing acetophenone, carbinol, phenol and higher boiling compounds.

2. A process according to claim 1 wherein said column is operated at atmospheric pressure.

3. A process according to claim 1 wherein said crude phenol is removed from said column as a liquid sidestream fraction.

4. A process according to claim 1 wherein said catalyst-free cumene hydroperoxide cleavage reaction product is almost completely vaporised prior to being fed to said column.

5. A process according to claim 4 wherein vaporisation is carried out in a plurality of stages in which each stage is effected at a progressively increasing temperature, the first stage being carried out at a temperature above the boiling point of acetone but below the boiling point of phenol to give a vapour fraction mainly consisting of compounds boiling below phenol, including a substantial proportion of acetone and containing in addition traces of acetophenone plus carbinol as well as phenol, said vapour fraction being fed directly to said column at a point in said column above said crude phenol sidestream fraction removal point, and a residue fraction, said residue fraction being passed to a second vaporisation stage maintained at a temperature above the boiling point of phenol to give a vapour fraction containing the bulk of the phenol and an unvaporised portion containing crackable high boiling compounds, said vapour fraction containing the bulk of the phenol being fed to said column at a point in the base region of said lower section thereof.

6. A process according to claim 5 wherein said unvaporised portion from said second vaporisation stage is pyrolised at a temperature above about 300° C. and the decomposition products of said pyrolysis fed to said column.

7. A process according to claim 5 wherein crackable high-boiling compounds selected from ortho-cumyl phenols, para-cumyl phenols and alpha-methyl styrene dimers present in said unvaporised portion from said second stage vaporisation are removed therefrom and fed to said distillation column at the same point as said vapour fraction containing the bulk of the phenol.

8. A process according to claim 7 wherein said crackable high boiling compounds are removed from said second vaporisation stage by stripping under reduced pressure.

9. A process according to claim 5 wherein said unvaporised portion from said second vaporisation stage is submitted to a wash treatment to remove the bulk of any salts present therein and is thereafter fed to said column.

10. A process according to claim 5 wherein the base of the distillation column is extended below said feed point of said vapor fraction containing the bulk of the phenol to provide a stripping section, and crude acetophenone is withdrawn as a secondary sidestream fraction from a point towards the bottom of said extended section, thereby allowing concentration of the remaining high-boilers in said reboiler at the bottom of said column.

11. A process according to claim 10 wherein a cracking catalyst is introduced into said reboiler maintained at a temperature in the range 250° to 300° C.

12. A process according to claim 11 wherein said cracking catalyst is phosphoric acid in a concentration of about 0.1 wt %.

13. A process according to claim 7 wherein said crackable high boiling compounds are removed from said second vaporisation stage by stripping in the presence of an inert gas.